(12) United States Patent
Riley

(10) Patent No.: US 8,075,849 B2
(45) Date of Patent: Dec. 13, 2011

(54) MEDICAL INSTRUMENT RETAINER ASSEMBLY AND METHOD OF MAKING THE RETAINER

(75) Inventor: Edward D. Riley, Auburn, ME (US)

(73) Assignee: Symmetry Medical Manufacturing, Inc., Warsaw (IN)

( * ) Notice: Subject to any disclaimer, the term of this patent is extended or adjusted under 35 U.S.C. 154(b) by 58 days.

(21) Appl. No.: 12/764,395

(22) Filed: Apr. 21, 2010

(65) Prior Publication Data

US 2010/0200444 A1      Aug. 12, 2010

Related U.S. Application Data

(62) Division of application No. 11/299,505, filed on Dec. 12, 2005, now Pat. No. 7,722,837.

(51) Int. Cl.
*A61L 2/00* (2006.01)
*A61L 9/00* (2006.01)
*A47F 7/00* (2006.01)
*A47G 29/00* (2006.01)
*B65D 83/10* (2006.01)

(52) U.S. Cl. ........ 422/300; 422/292; 422/297; 206/363; 206/368; 206/369; 206/370; 211/13.1; 211/86.13

(58) Field of Classification Search .................. 422/300, 422/292, 297; 211/85.13, 13.1; 206/363, 206/368, 369, 370, 263
See application file for complete search history.

(56) References Cited

U.S. PATENT DOCUMENTS

| | | | | |
|---|---|---|---|---|
| 5,098,676 | A * | 3/1992 | Brooks, Jr. | 422/292 |
| 5,467,874 | A * | 11/1995 | Whitaker | 206/378 |
| 5,827,487 | A * | 10/1998 | Holmes | 422/297 |
| 6,365,115 | B1 * | 4/2002 | Wood | 422/292 |
| 6,436,357 | B1 * | 8/2002 | Frieze et al. | 422/300 |

\* cited by examiner

*Primary Examiner* — Sean E Conley
*Assistant Examiner* — Regina M. Yoo
(74) *Attorney, Agent, or Firm* — Hayes Soloway P.C.

(57) ABSTRACT

A retainer assembly for retaining a medical device in a container having a perforated wall includes a retainer with a rigid support portion having at least one leg and a flexible, resilient instrument holding portion intimately bonded to the support portion so that the retainer is devoid of cracks and crevices between said portions. Each leg has a free end and an axial passage extending into the leg from that end so that the retainer may be positioned on the container wall with each opening in register with a perforation therein. A fastener extends into the passage of each leg and the underlying perforation from below the wall to anchor each leg to the wall under pressure thereby providing a seal between each leg and the wall. Various retainer embodiments and a method for making same are also disclosed.

17 Claims, 3 Drawing Sheets

STEP 1
MOLD SUPPORT

STEP 2
INJECTION MOLD
SILICONE HOLDER
ONTO SUPPORT

STEP 3
CLEAN + PROFILE HOLDER

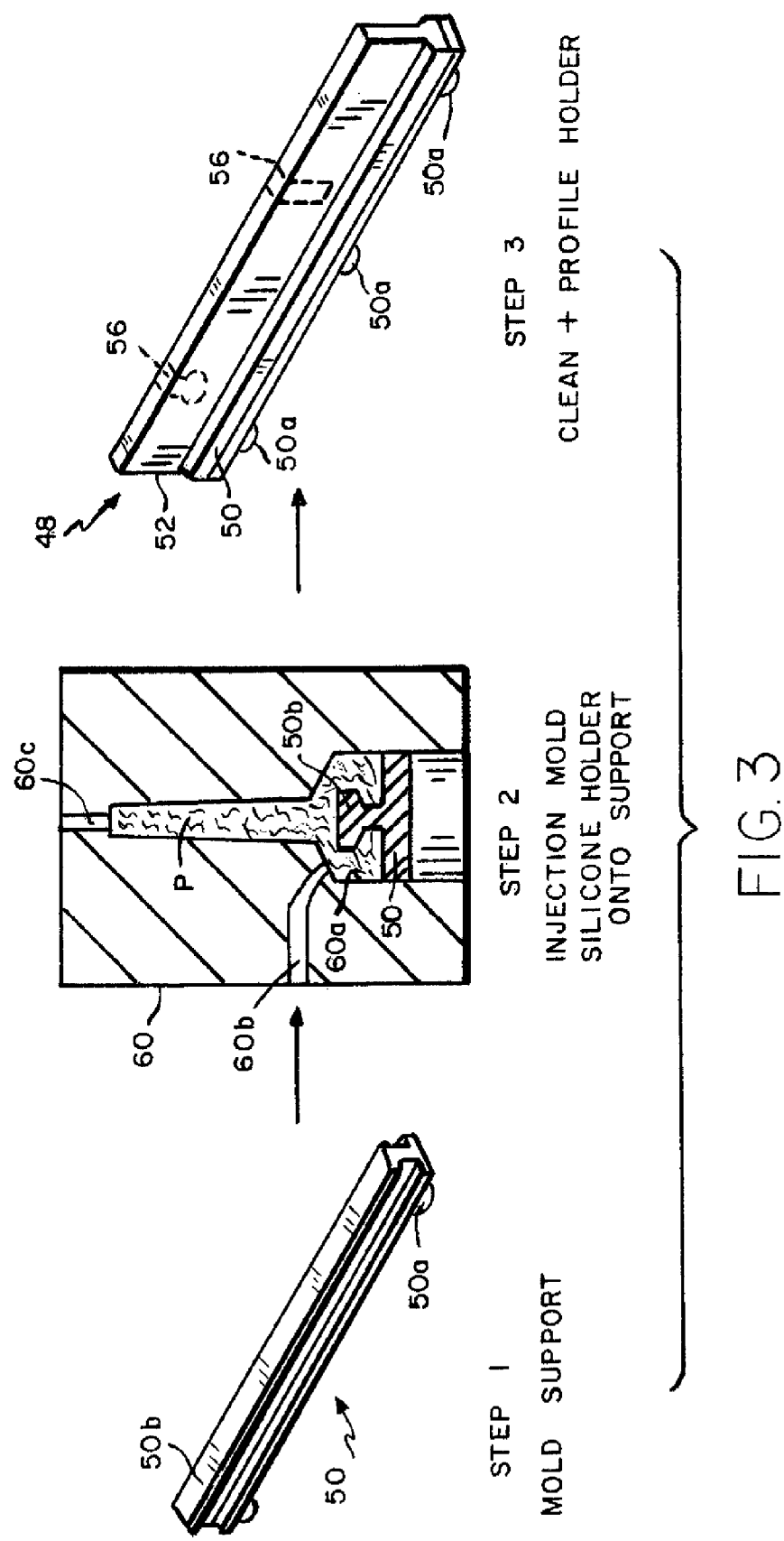

MEDICAL INSTRUMENT RETAINER ASSEMBLY AND METHOD OF MAKING THE RETAINER

This application is a divisional of co-pending application Ser. No. 11/299,505, filed Dec. 12, 2005.

BACKGROUND OF THE INVENTION

This invention relates to a retainer assembly for retaining medical instruments. It relates especially to a retainer assembly capable of holding medical instruments at fixed positions in a tray or other container while maintaining sterile conditions within the container.

There exists in the prior art various retainers and accessories for fixing the positions of articles of one kind or another. These include hooks, pegs, clips, brackets, etc. Such retainers may be used in a wide variety of applications. For example, they are commonly used in the medical field to fix the positions of various surgical instruments, devices and prostheses while those articles are being transported, sterilized and processed in one way or another. Accordingly, we will describe the invention in that context. It should be understood, however, that the present invention has application in other fields is besides the medical field.

Medical instruments are often transported in trays. Prior to use, such instruments are placed in the tray and subjected to sterilization. To improve the circulation of steam throughout the tray, the tray bottom wall and perhaps also the side wall are usually perforated. In order to maintain a separation between the various instruments in the tray, the instruments are supported or retained by posts, brackets or other retainers anchored to the tray. Following sterilization, the tray full of instruments may be transported to an operating room and placed close to a surgical team whose members may withdraw the instruments from the tray as needed for the particular surgical procedure being performed. Usually, the instruments are selectively arranged or organized in the tray so that they can be picked from the tray in the order in which they are needed for the particular procedure. Examples of such trays are disclosed in my patents U.S. Pat. Nos. 5,424,048 and 5,681,539.

FIG. 1 depicts a typical medical tray shown generally at 10. The tray has a bottom wall 10a and side walls 10b extending up from the bottom wall to define a generally rectangular interior space 12. The tray is usually made of a material able to withstand sterilization, e.g. polyphenylsulphone or a non-corroding metal such as aluminum, stainless steel or titanium. The bottom wall 10a of tray 10 is usually formed with a multiplicity of vent holes 16 arranged in columns and rows to allow for circulation of steam or other sterilizing fluid throughout the interior space 12. As will be described in more to detail presently, these holes may also function as anchoring points for the retainers and accessories used to locate various medical instruments within tray 10.

Tray 10 is adapted to contain a plurality of variously shaped medical instruments I. In order to retain these instruments in the tray, assorted retainers or accessories may be employed. These may include known solitary post assemblies 18 as well as conventional elongated retainer assemblies 20 and 20' having notches or slots for receiving instruments I as shown.

As depicted in FIGS. 1 and 2A, the retainer assembly 20 comprises a unitary retainer 22 molded of a rigid plastic material able to withstand sterilization. The retainer is in the form of an upstanding blade containing notches or slots 22a and having a bottom flange 24 so that the retainer has the general shape of an inverted letter T. Threaded holes 26 extend up from the bottom of retainer 22. These holes are spaced apart along the retainer a distance that is an integral multiple of the spacing between the holes 16 in a given row of holes in tray bottom wall 10a. Thus, retainer 22 may be positioned on the tray wall 10a with its holes 26 in alignment with the vent holes 16 in the tray so that the other components of the assembly 20, namely threaded fasteners 28, may be inserted through the vent holes and turned down into the registering holes 26 in retainer 22 as shown in FIG. 2A.

Instead of being a unitary part as depicted in FIG. 2A, some conventional retainers are composed of two separate pieces which are keyed together. A retainer such as this is shown generally at 22' in FIGS. 1 and 2B. That retainer comprises a rigid rail 32 molded of a suitable hard plastic material able to withstand sterilization. Spaced-apart threaded holes 34 extend up from the bottom of rail 32 for receiving threaded fasteners 28 to secure the rail to the tray bottom wall 10a in the same manner as retainer 22 described above.

Rail 32 is adapted to receive and support a blade-like instrument holder 38 made of a flexible, resilient, sterilizable material such as silicone. The holder 38 may be formed with slits or cut-outs 38a for holding medical instruments I. In order to mechanically secure the holder 38 to rail 32, the bottom of the holder is flanged to form a key 40 which is shaped and sized to slidably engage in a keyway 42 formed in the upper portion of rail 32.

The posts of assemblies 18 depicted in FIG. 1 may be anchored in a similar fashion to the tray bottom wall 10a using threaded fasteners 28.

Although these prior retainer assemblies perform their instrument retaining function satisfactorily, they may not pass new safety requirements being proposed by the FDA to ensure that medical trays and their contents are free from contamination. That is, more emphasis is being placed on being able to demonstrate the ability to thoroughly clean and sterilize such products. The FDA is particularly concerned with cleaning and sterilization at mating surfaces such as the undersurfaces of the retainer 22 and rail 32 where they meet the tray wall 10a, as well as the opposing surfaces at the boundary between the silicone holder 38 and the rail 32 of the retainer assembly 20' shown in FIG. 2B. If that holder 38 is flexed laterally, an appreciable may open between the holder and the rail. All of these locations have the possibility of trapping bacterial contamination and protecting same during the sterilization process. In fact, the only way to ensure a proper cleaning of these surfaces is to dissemble all of the retainer assemblies and remove them from the tray 10 so that all of the parts can be sterilized separately. Of course, all of the retainer parts must then be reassembled in the tray for the next operation. Needless to say, this is a tedious task and is not desirable from the standpoint of efficiency. Also, in their disassembled state, the various small parts may be misplaced or lost while being processed.

SUMMARY OF THE INVENTION

Accordingly the present invention aims to provide a retainer assembly for use in a medical tray or other container which minimizes the potential for bacterial contamination within the tray.

Another object of the invention is to provide a retainer assembly such as this which does not have to be separated from the tray in order to thoroughly clean and sterilize the tray and assembly components.

Yet another object of the invention is to provide a retainer assembly whose construction minimizes the likelihood of bacterial contamination in and around the assembly.

A further object is to provide a retainer consisting of a unitary part which may be rigidly anchored to a container wall while resiliently retaining various medical instruments placed in the container.

Still another object of the invention is to provide such a retainer which can be made in quantity relatively inexpensively using conventional molding or machining techniques.

Another object of the invention is to provide a method of making such a retainer having one or more of the above advantages.

Other objects of the invention will, in part, be obvious and will, in part, appear hereinafter.

The invention accordingly comprises the several steps and the relation of one or more of such steps with respect to each of the others, and the article possessing the features, properties and the relation of elements, all as exemplified in the following detailed description, and the scope of the invention will be indicated in the claims.

In general, the present retainer assembly comprises an instrument retainer for placement in a container such as a medical tray, and fastening means for anchoring the retainer to a wall of that container at one or more anchoring points.

The retainer has at least one rigid exposed support portion each having at least one anchoring point for receiving a fastener and a flexible, resilient instrument holding portion bonded to each support portion so that the retainer is essentially a unitary part completely devoid of cracks and joints in which bacteria could develop and multiply. Thus, the retainer assembly provides both a secure mechanical attachment to the container and a holding portion which may be configured to resiliently engage and fix within the container a variety of differently shaped and sized medical instruments and devices.

As we shall see, when forming the retainer an intimate bond is obtained between the resilient holding portion and the rigid support portion of the retainer by positioning an already formed support portion in a mold and injection molding a holding portion directly onto and around the support portion so that the two portions become as one. After the molding process, the holding portion may be cleaned and profiled to support various medical instruments and devices.

As will be described in more detail later, the holding portion of the retainer may be in the form of an elongated slotted blade designed to engage around or receive the medical instruments or it may be in the form of a fence or post positioned to corral instruments placed in the container. In each case, the holding and support portions of the retainer are intimately bonded together to minimize any possibility of bacterial in-growth thereon.

In a preferred embodiment of the invention, the retainer has an integral seal at each anchoring point thereof which, when the retainer is anchored to the container wall, surrounds the fastener at the corresponding anchoring point thus preventing in-growth of bacteria between the retainer and the container wall at that anchoring point. If a particular retainer has more than one anchoring point, the retainer is preferably shaped so that its anchoring points extend below the remainder of the retainer so that when the retainer is anchored to the container wall by the fasteners, each seal seats against the container wall. In one preferred embodiment of the invention, the seal is a knife edge depending from the support portion and encircling the fastener to provide a high pressure line contact between the support portion of the retainer and the container wall. In a second preferred embodiment of the invention, the seal is an extension of the holder portion of the retainer which extension forms a flexible resilient line contact seal around the fastener. Both seals prevent the infiltration of bacteria at the interface between the retainer and the container wall.

It is a further feature of the invention that the present retainers can be made relatively inexpensively in quantity using standard molding or machining techniques. Therefore they should be comparable in cost to conventional retaining devices which do not have the same advantages in terms of ease of use and freedom from bacterial build up.

BRIEF DESCRIPTION OF THE DRAWINGS

For a fuller understanding of the nature and objects of the invention, reference should be made to the following detailed description taken in connection with the accompanying drawings, in which:

FIG. 3 is a schematic diagram showing the steps for making the retainer component of a retainer according to the present invention;

DETAILED DESCRIPTION OF PREFERRED EMBODIMENTS

Figure 1:
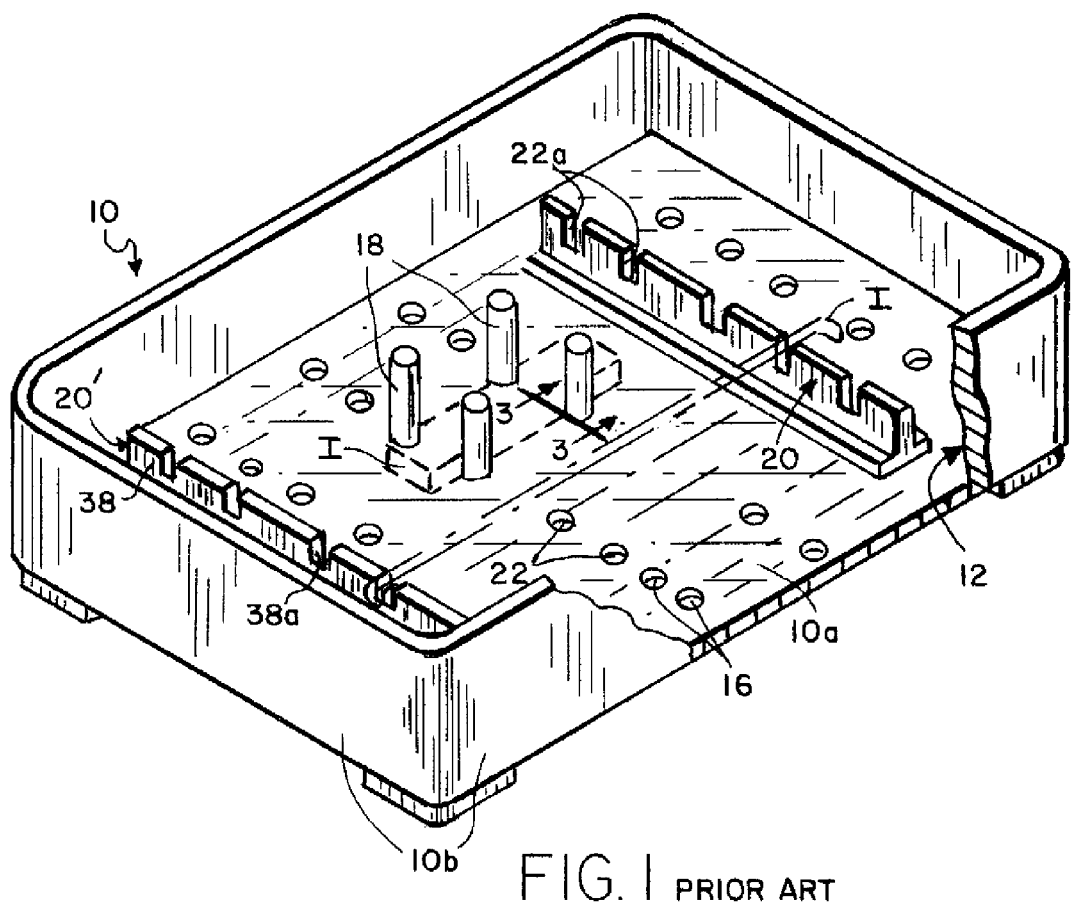
FIG. 1, already described, is a perspective view with parts broken away showing conventional retainer assemblies installed in a medical tray.
Figure 4A:
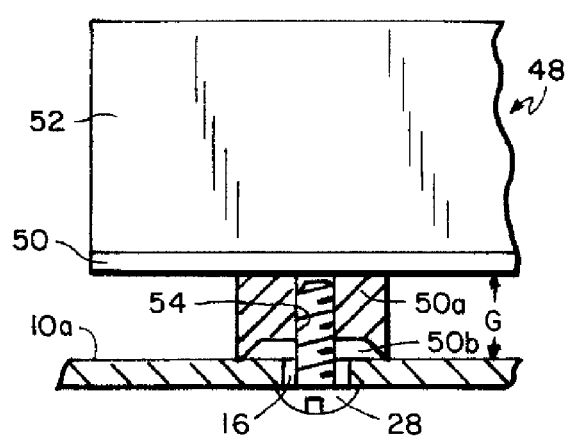
FIG. 4A is a fragmentary elevational view on a larger scale and with parts in section showing a retainer made in accordance with FIG. 3 and assembled to a container.
Figure 4B:
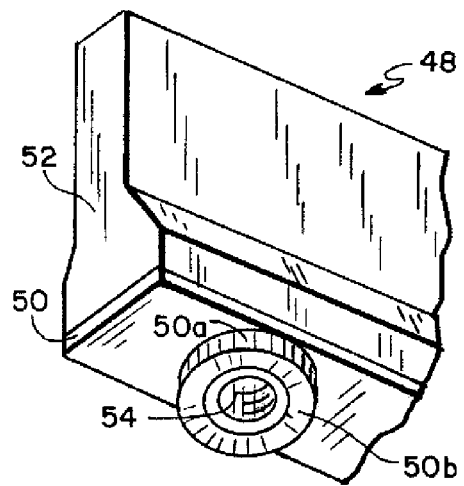
FIG. 4B is a fragmentary perspective view of the retainer in the FIG. 4A assembly.

Referring to FIGS. 4A and 4B and the right hand side of FIG. 3, my improved retainer shown generally at 48 comprises a rigid support portion 50 in the form of an elongated beam and an upstanding flexible resilient blade-like instrument holding portion indicated at 52 which is intimately bonded to support portion 50. The support portion includes one or more legs 50a each of which extends below portion 50 per se to provide an anchoring point. As best seen in FIGS. 4A and 4B, each leg 50a is formed with a threaded passage 54 which extends in from the lower end of the leg for anchoring the retainer to the wall of a container such as the bottom wall 10a of the medical tray illustrated in FIG. 1. For this, each leg 50a is located on base portion 50 so that it can be placed in register with a hole 16 in tray wall 10a. This enables a fastener 28 to be inserted from below the tray through that registering hole and screwed into the passage 54 in the corresponding leg 50a. Of course, if the retainer legs 50a do not line up with the holes 16 in the tray wall, additional such holes may be drilled through that wall at the appropriate places to accommodate the retainer. In any event, when the retainer is anchored to the tray wall 10a by fasteners 28, the retainer assembly is complete.

Figure 2A:
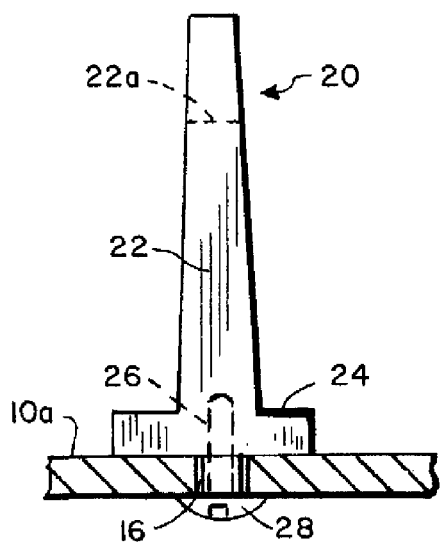
FIGS. 2A and 2B are elevational views of the known retainer assemblies shown in FIG. 1.
Figure 2B:
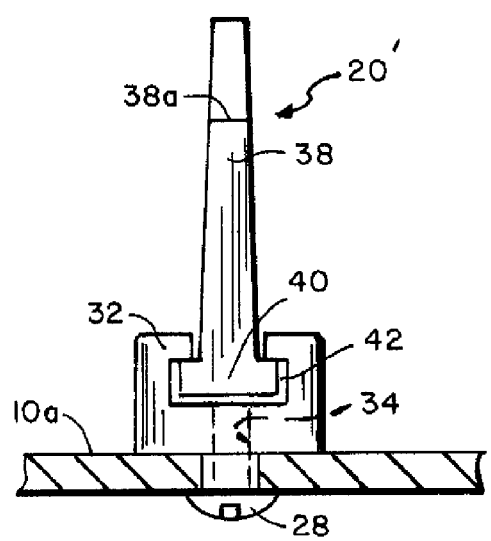

Although superficially the present retainer 48 appears similar to some prior instrument retaining brackets of this general type such as the one depicted in FIG. 2B, it differs in several important respects. More particularly, the support portion 50 of the present retainer 48 is actually used to help form the holding portion 52 thereof.

More particularly, as shown in FIG. 3, in a first step, the rigid support portion 50 is formed of a suitable sterilizable plastic or metal using a conventional molding or machining process. It is made not only with one or more legs 50*a*, but also with an integral upstanding rail 50*b* with which the holding portion 52 will interfit. Since the illustrated support portion 50 is in the form of an elongated beam, the rail in crosssection resembles the letter T. Of course, the rail 50*b* may be otherwise shaped to interfit with holding portion 52 as will be described. For example, portion 52 may comprise a column of spaced-apart upstanding posts or barbs.

In any event, after the support portion 50 is formed, in a second step, that portion is placed in a mold 60 having a cavity 60*a* shaped to accommodate support portion 50 so that that portion constitutes one wall of the cavity and so that the rail 50*b* of portion 50 projects into the cavity. The mold 60 may be of any standard design having an injection port 60*b* for injecting a plastic material P into cavity 60*a* that cavity being shaped to form the instrument holding portion 52 of the retainer. Preferably, the mold includes a vent passage 60*c* to vent air from cavity 60*a* as the cavity is being filled with plastic material.

The plastic material P may be any material conventionally used to resiliently hold medical instruments and devices, the preferred material being silicone.

During the injection molding process, the plastic material P is deposited to directly onto and around the bonding surfaces of the support portion 50 exposed in mold cavity 60*a*. Thus an intimate bond is formed between the plastic P and those surfaces. Resultantly, when the molding process is completed and the support portion is removed from mold 60, the plastic material P that has formed the holding portion 52 of the retainer is not only mechanically anchored to the rail 50*b* of support portion 50, but also it is intimately bonded to the bonding surfaces of that portion so that the retainer is completely devoid of any gaps, cracks or crevices that could provide refuge for bacteria and other contaminants.

After the injection molding step has been completed, the molded product may be cleaned and its holding portion 52 profiled, in a third step, to form the desired instrument retaining slots and notches 56 using a conventional water jet or die-cutting process.

The present retainer differs from others also in that its leg(s) 50*a* extend well below support portion 50 and holding portion 52. Also, the leg(s) in crosssection are larger than the holes 16 in tray wall 10*a*. Resultantly, when the retainer is anchored to the tray wall 10*a* as shown in FIG. 4A, the leg(s) act as spacers so that a relatively large gap G exists between the retainer per se and the tray wall. In other words, the retainer only contacts the tray wall directly underneath the leg(s) 50*a* so that when the tray and its contents are being sterilized, the sterilizing fluid can circulate underneath the retainer per se so that there can be no bacterial build up there.

As for the small areas underneath the retainer legs 50*a*, it has been found that these areas do not tend to trap contamination because each leg 50*a* is held against the tray wall 10*a* under relatively high contact pressure due to the associated fastener 28. However, in a preferred embodiment of the invention, an especially high contact pressure engagement of each leg 50*a* with the tray wall 10*a* is assured by forming each leg end with a depending circular knife edge 50*b* at the perimeter of leg 50*a* and which surrounds the fastener hole 54 as shown in FIGS. 4A and 4B. Thus when the associated fastener 28 is turned down into hole 54, the knife edge 50*b* is urged against the tray wall 10*a* under very high pressure due to its small contact area so that there is no possibility of biological contaminants passing between the leg and the container wall.

Figure 5:
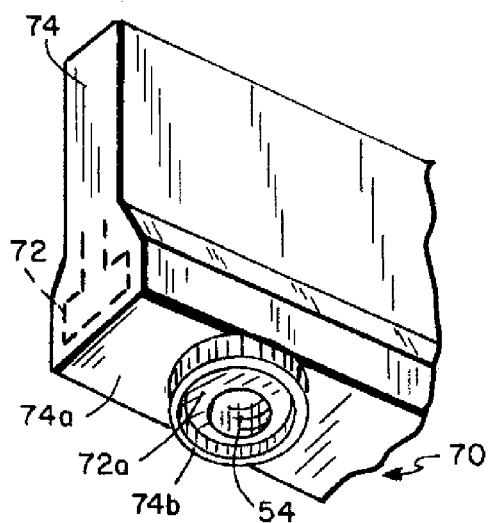
FIG. 5 is a similar view showing another retainer embodiment.

Refer now to FIG. 5 which shows another retainer embodiment indicated at 70 in which a support portion 72 of the retainer is fully encapsulated within a holding portion 74 except for the undersurface of each leg 72*a* of the support portion. In other words, the holding portion 74 is injection molded around support portion 72 so that a wall 74*a* of the holding portion extends under the support portion and around the side of each leg 72*a*. Preferably also, that wall extends beyond the end of each leg to form a flexible resilient lip or flange 74*b* as shown in FIG. 5. Thus, when the retainer is positioned in the tray 10 and anchored to the tray wall 10*a* by fasteners 28 as in FIG. 1, each flexible resilient lip 74*b* is drawn against the tray wall forming a resilient knife edge seal around the associated fastener which prevents the introduction of contaminants at each anchoring point of the retainer to the tray wall.

Figure 6:
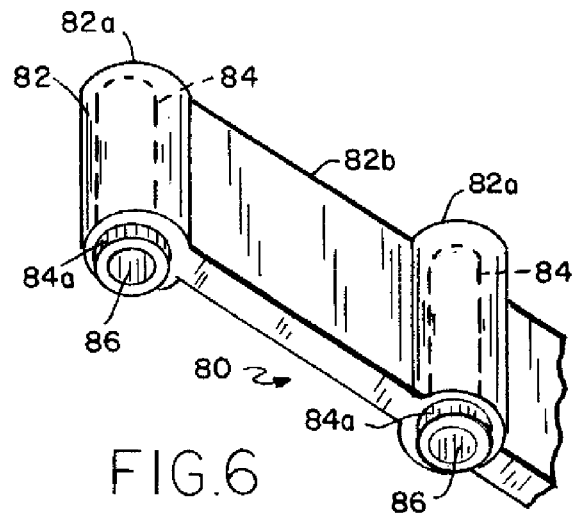
FIG. 6 is a perspective view illustrating still another retainer embodiment.

FIG. 6 illustrates yet another retainer embodiment shown generally at 80. In this case, the flexible, resilient instrument holding portion 82 comprises a pair of sleeves 82*a* injection molded around a pair of spaced-apart rigid posts 84 with a web 82*b* extending between the two sleeves. The posts 84 comprise the holding portion of this retainer. Preferably, the posts have ends 84*a* which extend beyond or below the lower ends of sleeves 82*a* and threaded fastener holes 86 extend in from those post ends. Thus, when retainer 80 is secured to tray wall 10*a* by fasteners 28 in the manner of retainer 48 described above, the holding portion 82 thereof is spaced above the tray wall. Also of course, the projecting ends 84*a* of posts 84 may be formed with a sealing flange similar to flange 50*b* on retainer 48 described above and shown in FIGS. 4A and 4B. Alternatively, the sleeves 82*a* may extend down around the post ends 84*a* to form a resilient seal similar to seal 74*b* described above in connection with retainer 70 in FIG. 5. In any event, when retainer 80 is secured to the tray wall 10*a*, it constitutes a fence or barrier which may be used to restrain or corral a medical instrument or device within the tray 10.

Of course, other fasteners may be used in my retainer assembly to anchor the various retainer embodiments to the container wall. For example, the retainers may be permanently anchored to the tray by rivets. Also, to accommodate trays having different wall thicknesses, the assembly may include the fastening means of the type disclosed to in my application Ser. No. 11/177,541, filed Jul. 8, 2005, the contents of which are hereby incorporated by reference herein.

Figure 7:
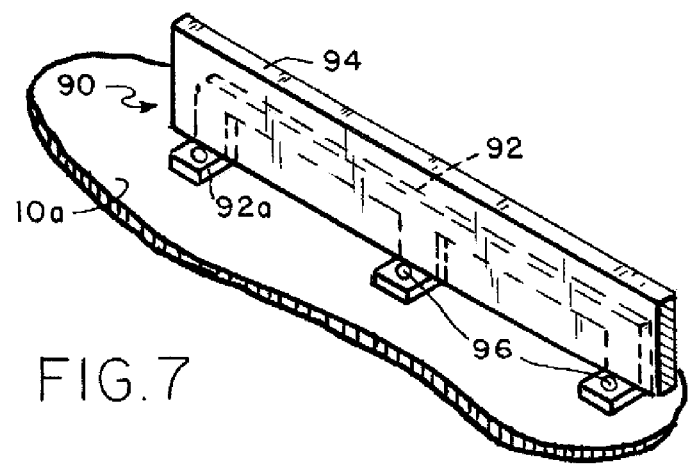
FIG. 7 is a perspective view on a smaller scale illustrating yet another embodiment of the invention.

FIG. 7 shows generally at 90 another retainer embodiment having a rigid support portion 92 onto which is injection molded a flexible resilient instrument holding portion 94. Support portion 92 may be a stamped metal part formed with one or more legs 92*a* which extend from an edge of holding portion 94. These legs may be used to anchor the retainer to container wall 10*a* by inserting fasteners 96 e.g. screws, rivets or friction pins, through the legs and the wall. As with the other retainer embodiments, the holding portion 94 forms an intimate bond with the support portion 92 so that the retainer is devoid of potential contamination sites.

Thus the present retainer assemblies provide a rigid connection to the container wall and a resilient engagement with the medical instruments which they retain. Yet they are devoid of joints and interfaces which could be sites for bacterial infestation. Retainer assemblies made in accordance with this invention can remain in place in a medical tray or other container during sterilization with assurance that after the sterilization process is completed, the tray and its contents will be clean and free of bacterial contamination and will conform to any standards imposed by FDA. This ability to leave the retainer(s) in the tray will make the sterilization process much more efficient and will free up medical personnel to do other important tasks.

It will thus be seen that the objects set forth above, among those made apparent from the preceding description, are efficiently attained. Also, certain changes may be made in carrying out the above method and in the constructions set forth without departing from the scope of the invention. For example, retainers in the form of silicone sheathed posts similar to posts 18 in FIG. 1 may be made according to this invention simply eliminating the web 82*b* when molding the sleeves 82*a* of the FIG. 6 retainer. Therefore, it is intended that all matter contained in the above description and shown in the accompanying drawings shall be interpreted as illustrative and not in a limiting sense.

It is also to be understood that the following claims are intended to cover all of the generic and specific features of the invention described herein.

The invention claimed is:

1. A retainer for retaining a medical device in a container having a wall with perforations, said retainer comprising:
    a rigid support portion to provide at least one bonding surface, at least one leg extending from the bonding surface and an axial passage extending into said leg from a free end thereof so that the retainer may be positioned on said wall with each axial passage in register with a perforation in said wall, wherein said wall is contacted by said leg only at a surface directly underneath said leg, and injection molding a plastic material directly onto said bonding surface to form a flexible resilient instrument holding portion which extends from the support portion in a direction opposite to that of said at least one leg so that the retainer is devoid of cracks and crevices which could be potential sites for bacterial in-growth; and
    a seal between each leg and the wall.

2. The retainer defined in claim 1 wherein the support portion is formed as a post and the holding portion is formed as a sleeve encircling the post.

3. The retainer defined in claim 1 wherein the support portion is formed as a beam and the holding portion is formed as a blade that is coextensive with the beam.

4. The retainer defined in claim 1 wherein the support portion is formed as a pair of spaced-apart parallel posts and the holding portion is formed as a pair of sleeves encircling the posts with a web connecting the sleeves.

5. The retainer defined in claim 1 wherein each leg is formed with a peripheral knife edge at the free end thereof.

6. The retainer defined in claim 1 wherein said holding portion includes a wall extension encircling each leg.

7. The retainer defined in claim 6 wherein the wall extension encircling each leg protrudes beyond the free end of that leg to form a flexible resilient sealing lip at the periphery of said free end.

8. The retainer defined in claim 1 wherein the holding portion includes one or more cutouts.

9. A method of making a retainer for retaining medical devices in a container having a wall with perforations, said method comprising the steps of:
    forming a rigid support portion to provide at least one bonding surface, at least one leg extending from the bonding surface and an axial passage extending into said leg from a free end thereof so that the retainer may be positioned on said wall with each axial passage in register with a perforation in said wall, wherein said wall is contacted by said leg only at a surface directly underneath said leg, and injection molding a plastic material directly onto said bonding surface to form a flexible resilient instrument holding portion which extends from the support portion in a direction opposite to that of said at least one leg so that the retainer is devoid of cracks and crevices which could be potential sites for bacterial in-growth; and
    providing a seal between each leg and the wall.

10. The method of claim 9, further comprising the step of cutting one or more slots in said holding portion.

11. The method of claim 9, further comprising the step of forming the support portion as a post and the holding portion as a sleeve encircling the post.

12. The method of claim 9, further comprising the step of forming the support portion as a beam and the holding portion as a blade that is coextensive with the beam.

13. The method of claim 9, further comprising the step of forming the support portion as a pair of spaced-apart parallel posts and the holding portion as a pair of sleeves encircling the posts with a web connecting the sleeves.

14. The method of claim 9, further comprising the step of forming each leg with a peripheral knife edge at the free end thereof.

15. The method of claim 9, further comprising the step of forming the holding portion with a wall extension encircling each leg.

16. The method of claim 15, wherein the wall extension encircling each leg protrudes beyond the free end of that leg, thereby forming a flexible resilient sealing lip at the periphery of said free end.

17. The method of claim 9, further comprising the step of forming at least one cutout within the holding portion.

* * * * *